(12) United States Patent
Fischer, Jr. et al.

(10) Patent No.: US 7,400,445 B2
(45) Date of Patent: Jul. 15, 2008

(54) OPTICAL FILTERS FOR ACCELERATED WEATHERING DEVICES

(75) Inventors: Richard M. Fischer, Jr., Hudson, WI (US); Warren D. Ketola, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 111 days.

(21) Appl. No.: 11/141,589

(22) Filed: May 31, 2005

(65) Prior Publication Data

US 2006/0268401 A1    Nov. 30, 2006

(51) Int. Cl.
*G06K 7/10* (2006.01)
(52) U.S. Cl. ........................ 359/350; 359/355
(58) Field of Classification Search .......... 359/350–359
See application file for complete search history.

(56) References Cited

U.S. PATENT DOCUMENTS

| | | | |
|---|---|---|---|
| 3,202,811 A | 8/1965 | Hall, Jr. | |
| 4,125,775 A | 11/1978 | Chodak | |
| 4,487,904 A | 12/1984 | Fukuda et al. | |
| 4,542,449 A | 9/1985 | Whitehead | |
| 4,568,445 A | 2/1986 | Cates et al. | |
| 4,721,377 A | 1/1988 | Fukuda et al. | |
| 4,747,645 A | 5/1988 | Rudzki | |
| 4,812,032 A | 3/1989 | Fukuda et al. | |
| 4,820,326 A | 4/1989 | Speit | |
| 4,931,523 A | 6/1990 | Watanabe et al. | |
| 4,931,655 A | 6/1990 | Yoshida et al. | |
| 4,937,172 A | 6/1990 | Gervay | |
| 4,962,163 A | 10/1990 | Hefner, Jr. et al. | |
| 4,970,135 A | 11/1990 | Kushi et al. | |
| 5,066,750 A | 11/1991 | Hefner, Jr. et al. | |
| 5,149,776 A | 9/1992 | Kushi et al. | |
| 5,164,464 A | 11/1992 | Hefner, Jr. et al. | |
| 5,175,030 A | 12/1992 | Lu et al. | |
| 5,183,597 A | 2/1993 | Lu | |
| 5,183,870 A | 2/1993 | Fukushima et al. | |
| 5,220,840 A | 6/1993 | Neigoff et al. | |
| 5,247,038 A | 9/1993 | Fukushima et al. | |
| 5,354,821 A | 10/1994 | Huver et al. | |
| 5,424,339 A | 6/1995 | Zanka et al. | |
| 5,486,949 A | 1/1996 | Schrenk et al. | |
| 5,612,820 A | 3/1997 | Schrenk et al. | |
| 5,626,800 A | 5/1997 | Williams et al. | |
| 5,665,494 A | 9/1997 | Kawabata et al. | |
| 5,691,846 A | 11/1997 | Benson, Jr. et al. | |

(Continued)

FOREIGN PATENT DOCUMENTS

EP    0 089 041    11/1987

(Continued)

OTHER PUBLICATIONS

WG-320 Analysis.

(Continued)

*Primary Examiner*—Joshua L Pritchett
(74) *Attorney, Agent, or Firm*—Carolyn A. Fischer

(57) ABSTRACT

Optical filters comprising a small concentration of visible light absorbing components optionally in combination with small concentrations of ultraviolet and infared absorbing components suitable for use in an illuminator for an accelerated weathering device and methods of accelerated weathering.

20 Claims, 5 Drawing Sheets

U.S. PATENT DOCUMENTS

| | | | |
|---|---|---|---|
| 5,714,218 A | 2/1998 | Nishio et al. | |
| 5,760,126 A | 6/1998 | Engle et al. | |
| 5,771,328 A | 6/1998 | Wortman et al. | |
| 5,783,120 A | 7/1998 | Ouderkirk et al. | |
| 5,825,543 A | 10/1998 | Ouderkirk et al. | |
| 5,828,488 A | 10/1998 | Ouderkirk et al. | |
| 5,882,774 A | 3/1999 | Jonza et al. | |
| 5,898,523 A | 4/1999 | Smith et al. | |
| 5,908,874 A | 6/1999 | Fong et al. | |
| 5,917,664 A | 6/1999 | O'Neill et al. | |
| 5,919,551 A | 7/1999 | Cobb, Jr. et al. | |
| 5,932,626 A | 8/1999 | Fong et al. | |
| 5,948,514 A | 9/1999 | Komori et al. | |
| 6,107,364 A | 8/2000 | Fong et al. | |
| 6,111,696 A | 8/2000 | Allen et al. | |
| 6,218,074 B1 | 4/2001 | Dueber et al. | |
| 6,225,244 B1 | 5/2001 | Oguma | |
| 6,280,063 B1 | 8/2001 | Fong et al. | |
| 6,291,070 B1 | 9/2001 | Arpac et al. | |
| 6,329,058 B1 | 12/2001 | Arney et al. | |
| 6,355,754 B1 | 3/2002 | Olson et al. | |
| 6,356,391 B1 | 3/2002 | Gardiner et al. | |
| 6,359,170 B1 | 3/2002 | Olson | |
| 6,368,682 B1 | 4/2002 | Fong | |
| 6,376,590 B2 | 4/2002 | Kolb et al. | |
| 6,376,704 B1 | 4/2002 | Olson | |
| 6,432,526 B1 | 8/2002 | Arney et al. | |
| 6,514,842 B1 | 2/2003 | Prall et al. | |
| 6,521,677 B2 | 2/2003 | Yashiro et al. | |
| 6,541,591 B2 | 4/2003 | Olson et al. | |
| 6,593,392 B2 | 7/2003 | Wang | |
| 6,604,436 B1 | 8/2003 | Lewandowski et al. | |
| 6,656,990 B2 | 12/2003 | Shustack et al. | |
| 6,727,309 B1 | 4/2004 | Paiva et al. | |
| 6,859,309 B2 | 2/2005 | Fischer, Jr. et al. | |
| 7,038,196 B2 | 5/2006 | Scott et al. | |
| 2002/0123589 A1 | 9/2002 | Olson et al. | |
| 2003/0100693 A1 | 5/2003 | Olson et al. | |
| 2003/0129385 A1 | 7/2003 | Hojo et al. | |
| 2003/0133184 A1* | 7/2003 | Fischer et al. | 359/361 |
| 2003/0165680 A1 | 9/2003 | Brady et al. | |
| 2003/0175004 A1 | 9/2003 | Garito et al. | |
| 2003/0180029 A1 | 9/2003 | Garito et al. | |
| 2004/0059013 A1 | 3/2004 | Tanabe et al. | |
| 2004/0132858 A1 | 7/2004 | Chisholm et al. | |
| 2004/0229059 A1 | 11/2004 | Kausch et al. | |
| 2004/0233520 A1* | 11/2004 | Ketola et al. | 359/361 |
| 2004/0233526 A1 | 11/2004 | Kaminsky et al. | |
| 2005/0059766 A1 | 3/2005 | Jones et al. | |
| 2005/0225847 A1* | 10/2005 | Ketola et al. | 359/361 |

FOREIGN PATENT DOCUMENTS

| | | |
|---|---|---|
| EP | 1 014 113 | 6/2000 |
| WO | WO 96/19347 | 6/1996 |
| WO | WO 98/50340 | 12/1998 |
| WO | WO 00/06495 | 2/2000 |
| WO | WO 00/14050 | 3/2000 |
| WO | WO 01/29138 | 4/2001 |
| WO | WO 02/45129 | 6/2002 |
| WO | WO 03/033558 | 4/2003 |
| WO | WO 03/076528 | 9/2003 |

OTHER PUBLICATIONS

Pending U.S. Appl. No. 10/870,366 filed Jun. 17, 2004.
Pending U.S. Appl. No. 11/078,145, filed Mar. 11, 2004.
Search Report.

* cited by examiner

OPTICAL FILTERS FOR ACCELERATED WEATHERING DEVICES

BACKGROUND

Often a manufacturer will warranty a product used outdoors for a specified lifetime. Accelerated weathering devices are used by a number of industries to test a product's performance after exposure to outdoor environmental conditions such as temperature cycles, moisture including humidity, condensation, and rain, as well as exposure to (i.e. simulated) solar radiation. Although all such stresses can result in product degradation, exposure to solar radiation is one of the more influential factors in weathering because ultraviolet rays often tend to break down polymers and other materials over time.

Among the more difficult tasks in the manufacture of accelerated weathering devices is to provide a spectral power distribution of artificial light that matches closely to that of natural sunlight at the earth's surface, i.e. terrestrial sunlight. This is typically accomplished by passing illumination from an artificial light source through one or more optical filters to filter out wavelengths of light that are not present in actual sunlight. By matching or closely approximating the spectral power distribution of natural sunlight, the results of exposure to the accelerated weathering device will more closely approximate effects of real world exposure.

Commercially available optical filters often pass more amounts of ultraviolet radiation, at wavelengths less than 290 nm, than present in actual terrestrial solar radiation. Radiation at these wavelengths can cause materials, such as polyethylene terephthalate and polyurethanes prepared from phthalate containing polyols, to fail prematurely. Other commercially available optical filters transmit insufficient intensity of light within the solar spectrum. This can lead to slower degradation rates or longer test times.

U.S. Pat. No. 4,931,655 describes and apparatus for accelerated weather testing of a sample using a metal halide lamp. The optimum filter is described as being made of soft glass having a low melting point which consists of, for instance, $SiO_2$ of 60-65% (percentage by weight), Pb of 15-20%, Na of 7-8%, K of 7-8%, Co of 1%, and Ni of 1%.

U.S. Pat. No. 6,859,309 is directed to an optical filter for use in accelerating weathering device that exhibits certain irradiance ratios that approximate sunlight. A preferred optical filter includes a glass having a lead content of between 0.5% and 50% by weight that is free of visible light absorbing components. In some examples, the filter can be constructed to have a thickness of 0.7 mm to 10 mm. In another aspect, the optical filter is part of an optical filter that may further include an ultraviolet transmissive optical filter. The ultraviolet transmissive optical filter may be constructed from quartz glass and may further include an infrared absorbing coating.

SUMMARY

The exemplified optical filter of U.S. Pat. No. 6,859,309 was prepared from a glass that was free of visible light absorbing components. It has since been found that an optical filter can be prepared from a glass containing small concentrations of visible light absorbing components. The resulting filter has at least equivalent spectral distribution properties.

In one embodiment, an accelerated weathering device is described comprising a weathering fixture adapted to hold at least one product sample; an illuminator disposed proximate to the weathering fixture wherein the illuminator comprises a light source and an optical filter disposed proximate to the light source, the optical filter comprising at least one visible light absorbing component alone or in combination with one or more ultraviolet light absorbing components and infared absorbing components in a total amount of less than 0.5 wt-% based on elemental concentration of the optical filter and the remainder of the optical filter comprises one or more inorganic oxides that do not absorb visible or ultraviolet light.

In other embodiments, the invention relates to method of accelerated weathering with such illuminator. The illuminator and optical filter may be suitable for other uses. Accordingly, in other embodiments, the invention relates to the illuminator and optical filter.

The preferred optical filter exhibits certain spectral characteristics. In one aspect, the optical filter has a ratio of total irradiance for wavelengths ranging from 400 nm to 700 nm to total irradiance ranging from 290 nm to 800 nm of at least 0.6. In another aspect, illumination passed through the optical filter preferably has a first ratio of total irradiance for wavelengths shorter than 290 nm to total irradiance for wavelengths ranging from 300 nm to 400 nm of less than $2.0 \times 10^{-6}$, a second ratio of irradiance at 310 nm to total irradiance for wavelengths ranging from 300 nm to 400 nm of at least $1.2 \times 10^{-3}$, and a third ratio of total irradiance at wavelengths ranging from 400 nm to 700 nm to total irradiance at wavelengths ranging from 290 nm to 800 nm of at least 0.6. Illumination from the light source preferably includes an irradiance of ranging from about 0.3 W/m² to about 1.5 W/m² at 340 nm. In another aspect, illumination from the light source includes a spectral component of at least 290 nm to 400 nm. In another aspect, illumination passed through the optical filter comprises a cut-on wavelength of ranging from 290 nm to 300 nm; a first ratio of an irradiance at 310 nm to total irradiance for wavelengths ranging from 300 nm to 400 nm of at least $1.2 \times 10^{-3}$, and a second ratio of total irradiance at wavelengths ranging from 400 nm to 700 nm to total irradiance at wavelengths ranging from 290 nm to 800 nm of at least 0.6.

DETAILED DESCRIPTION

Figure 1:
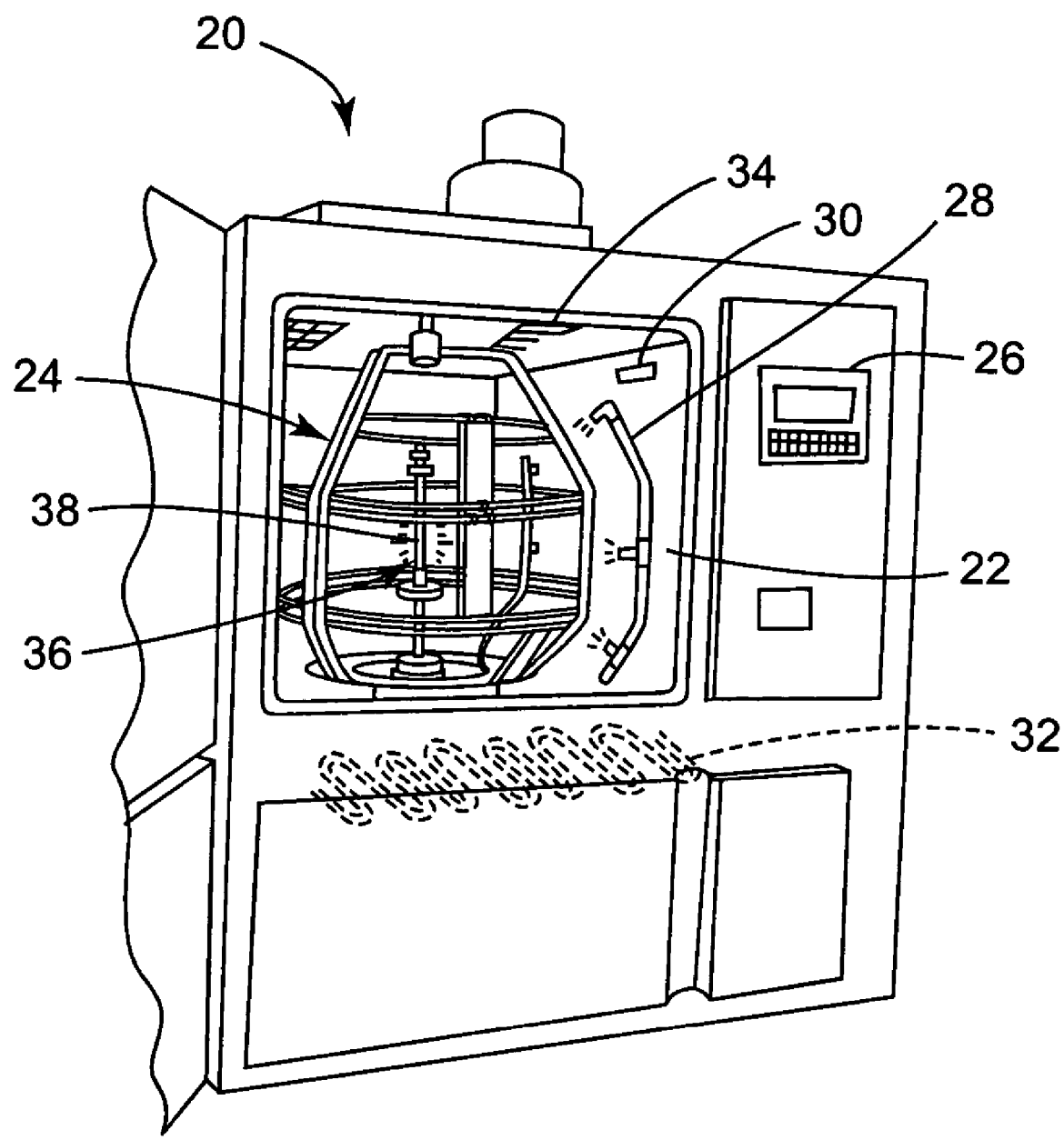
FIG. 1 shows a perspective view of an accelerated weathering device constructed in accordance with the invention.

Presently described are accelerated weathering devices, methods of accelerated weathering, illuminators, and optical filters. The illuminators and optical filters may be suitable for other uses.

Presently described is an optical filter comprised of glass having a low concentration of visible light absorbing optionally in combination with one or more ultraviolet light ("UV")

absorbing components and/or one or more infrared ("IR") absorbing components. The glass comprises at least a detectable amount of visible light absorbing and optionally UV and IR light absorbing components. For example, the optical filter may contain greater than 2 parts per million of light absorbing components or a concentration of greater than 0.0002% inorganic oxide. In addition the optical filter may further include greater than 2 parts per million UV absorbing component or a concentration of greater than 0.0002% inorganic oxide. Such concentrations can be detected with known laser ablation techniques. The concentration of the total amount of visible light absorbing and optionally UV and/or IR light absorbing components may be greater than 50 parts per million (i.e. elemental absorbing component) or greater than 0.005 wt-% inorganic oxide. The concentration of the total amount of elemental visible light absorbing components is typically less than 0.5 wt-%, less than 0.4 wt-%, less than 0.3 wt-%, less than 0.2 wt-%, or less than 0.1 wt-%. Various visible light absorbing are known including for example $Fe_2O_3$, $Cr_2O_3$, $Co_2O_3$, $Cu_2O$, $CuO$, $MnO$, $Mn_2O_3$, $V_2O_5$, $CeO_2$, $Sb_2O_3$, $SnO_2$, and $Nd_2O_3$. The presence of visible light absorbing inorganic oxides typically imparts color to glass beads. Various UV absorbing components are also known including for example $Cu_2O$, $CuO$, and $TiO_2$. $CuO$ is also a known IR absorbing component.

With the exception of the detectable amount of visible light absorbing and optional UV light absorbing component, the remainder of the optical filter comprises one or more inorganic oxides that provide a transparent glass. Accordingly, the remainder of the optical filter comprises one or more inorganic oxides that do not absorb visible light and/or UV light. In some embodiments the optical filter comprises at least 40 wt-% and typically no more than 80 wt-% silicon dioxide. The optical filter may also comprise potassium oxide and optionally sodium oxide in concentrations totaling up to about 30 wt-%.

The optical filter preferably comprises a lead content ranging from about 0.5% to about 50% wt-%. Such glass is also known as lead glass, and sometimes referred to as flint glass. The amount of lead in the optical filter depends on the thickness of the glass. For embodiments wherein the glass has a lead content of approximately 0.5% by weight, the filter will have a thickness of approximately 10 mm. For embodiments wherein the glass has a lead content of approximately 50% by weight, the filter will have a thickness of approximately 0.7 mm. In some embodiments, the lead ranges from about 25% to about 35% by weight, and the thickness of the optical filter ranges from about 1 to 2 mm. Although, optical filters can be constructed over a wide range of lead content, optical filters that are too thin can be less durable, whereas optical filters that are too thick are less economical.

An exemplary filter may comprise the following inorganic oxides.

|    |          | Element  | Oxide    |
|----|----------|----------|----------|
| Al | $Al_2O_3$ | 78 ppm  | 0.01%    |
| As | $As_2O_3$* | 0.10%  | 0.13%    |
| B  | $B_2O_3$ | 27 ppm   | 0.01%    |
| Ba | BaO      | ND       | ND       |
| Ca | CaO      | 62 ppm   | 0.01%    |
| K  | $K_2O$   | 4.40%    | 5.30%    |
| Mg | MgO      | <10 ppm  | <17 ppm  |
| Na | $Na_2O$  | 3.91%    | 4.18%    |
| Pb | PbO*     | 30.10%   | 32.21%   |
| Si | $SiO_2$  | 26.14%   | 55.94%   |

-continued

|    |          | Element  | Oxide    |
|----|----------|----------|----------|
| Ti | $TiO_2$  | 44 ppm   | 0.01%    |
| Zn | ZnO      | 80 ppm   | 0.01%    |
| Ni |          | 2-50 ppm |          |

*In the glasses, some of the metal oxides could be in different oxidation forms (for instance As could be in $As_2O_3$ or $As_2O_5$).

The optical filter is comprised of a glass at an appropriate thickness to filter illumination from a light source to approximate solar radiation. In general, irradiance is the radiant power per unit area, typically reported in watts per square meter ($W/m^2$). Two spectral regions are of primary interest for characterizing the optical filter. The first spectral region includes wavelengths shorter than 290 nm. Ultraviolet radiation less than 290 nm is high energy and causes rapid polymer degradation. Terrestrial solar ultraviolet light has very little radiation below 290 nm. The second spectral region includes irradiance at 310 nm. Terrestrial solar radiation is insignificant below 290 nm and becomes significant at about 300 nm. Thus, the solar cut-on wavelength typically ranges from 290 nm to 300 nm at midsummer at noon. Irradiance at 310 nm provides a realistic indication about whether the filtered light has sufficient irradiance in the region just above the solar cut-on to provide an effective test.

As used herein, "cut-on wavelength" is the shortest wavelength where irradiance is at least 0.001 $W/m^2$ when tested with a xenon-arc or metal halide light source. Test methods for determining the cut-on wavelength are susceptible to noise. In order to account for noise, the cut-on wavelength can also be defined as the wavelength where the measured irradiance is the fourth in succession of increasing integer wavelength with increasing irradiance and the minimum irradiance is 0.00002 $W/m^2$.

The optical filter is designed to satisfy various criteria. The concentration of light absorbing components and optional UV and/or IR components is present in low enough concentrations that the optical filter meets the following spectral distribution criteria. First, illumination from the light source passing through the optical filter, or filtered illumination, has a first ratio of total irradiance for wavelengths shorter than 290 nm to total irradiance for wavelengths ranging from 300 nm to 400 nm equal to or less than $2.0 \times 10^{-6}$. Typically, this first ratio is zero. Second, illumination from the light source passing through the optical filter has a ratio of irradiance at 310 nm to the second total irradiance (the total irradiance ranging from 300 nm to 400 nm) of greater than or equal to $1.2 \times 10^{-3}$. Typically this second ratio is no greater than 0.04. Total irradiance is the sum of the irradiance measured for each integer wavelength over a given range. A suitable method for determining total irradiance is to make measurements of irradiance at 2 nm increments, then add up the irradiance at each measured wavelength and multiply the resulting sum by 2. To calculate the first total irradiance, the sum of the irradiance measured from 250 nm to 288 nm at 2 nm increments is multiplied by 2. To calculate the second total irradiance, the sum of the irradiance measured from 300 nm to 400 nm at 2 nm increments is multiplied by 2.

In addition to these two criteria, it is preferred that the ratio of the total irradiance at wavelengths ranging from 400 nm and 700 nm in comparison to the total irradiance at wavelengths ranging from 290 nm to 800 nm is at least 0.6 or greater. For example this third ratio may be 0.7 and is typically no greater than about 0.8. This third criteria is typically met by employing a xenon-arc or metal halide light source.

The above criteria are preferably met over a large range of power supplied to the light source. For example the light source may provide an irradiance ranging from about 0.3 W/m² to about 1.5 W/m² at 340 nm. The use of higher irradiance than typical with the present filter provides faster test results by shortening the exposure time.

The optical filter described herein can be adapted to be employed in various known laboratory accelerated weathering test chamber devices such as available from Q-panel Lab Products, Cleveland, Ohio under the trade designations "Model Q-Sun Xe1 and Xe3" and from Atlas Material Testing Technology LLC, Chicago, Ill. Suntest under the trade designations "CPS/CPS+", "XLS/XLS+", and "XXL,XXL+", "Ci 35/65", "Ci 3000/4000/5000", "Xenotest 150+", and "Xenotest Alpha and Beta". Suga Test Instruments Co., Ltd, Tokyo, JP also distributes weathering devices.

FIG. 1 is a representative accelerated weathering device 20. The accelerated weathering device 20 includes a weathering chamber 22. Inside the weathering chamber 22 is a weathering fixture 24 adapted to hold a number of product samples (not shown) for testing. Exposure parameters are input through user-interface 26. Exemplary exposure parameters include moisture such as humidity, water spray, condensation, temperature, and irradiance. Mist generators 28 provide atomized water into the weathering chamber 22. Humidity within the chamber is measured via humidity sensor 30. Heater 32 generates heat within the chamber 22. Heat is measured with a temperature sensor 34. Signals received from the sensors 30, 34 are used to control or maintain the temperature and moisture stresses within the chamber 22. The weathering chamber 22 also includes an illumination assembly 36 that includes illuminator 38. The illumination assembly 36 provides and controls irradiance and works to cool illuminator 38. In the example shown, the illuminator 38 is disposed near the center of the weathering fixture 24 to provide irradiance to the product samples.

Use of such accelerated weathering devices generally includes providing at least one product sample proximate an illuminator in an accelerated weather device and radiating the product sample with the illuminator. Any product can be subjected to accelerated weathering. Products that are subject to exposure to outdoor environments are most commonly tested including for example paint, varnish, protective coating, plastic, textile, sign material (e.g. retroreflective), a roofing material, a siding material, a window treatment, an architectural ornament, tape, sealant, medication, adhesive, water proofing treatment. Generally one or more product performance tests are conducted prior to and after various durations of exposure. Representative tests include, for example, gloss, color shift, adhesion (cross hatch and peel strength), tensile and elongation, retroreflectance, haze, chemical changes detected by a range of analytical techniques (IR, UV/Visible spectrometry, etc.), visual appearance (cracking, delamination, adhesion failure, shrinkage), as well as any loss of intended function.

Figure 2:
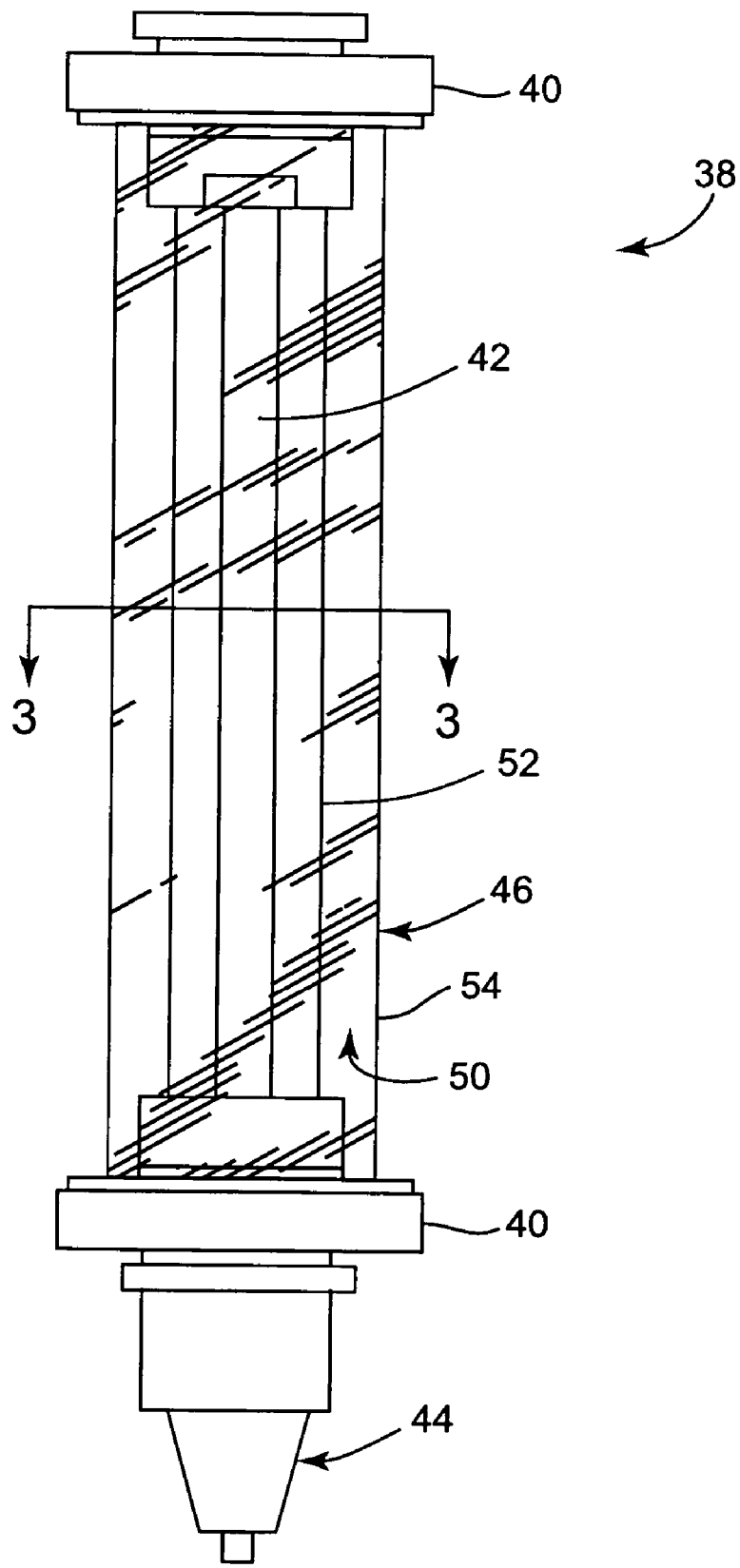
FIG. 2 shows a side view of an illuminator used within the accelerated weathering device of FIG. 1.

FIG. 2 shows one example of the illuminator 38. The illuminator 38 includes a pair of end caps 40 that couple and retain the light source 42. Plug 44 mates with a conductor in the illumination assembly 36 to provide power to the light source 42. The light source 42 is surrounded by at least one optical filter or, in the example shown, an optical filter assembly 46. An optical filter assembly is a plurality of optical filters. A coolant 50 flows through the illuminator 38 to control and maintain the temperature of the illuminator 38. Light source 42 includes a lamp having spectral emissions at least in the range of 200 nm to 700 nm. Examples of known light sources suitable for use in accelerated weathering devices include carbon-arc lamps, xenon-arc lamps, metal halide lamps, fluorescent lamps, and the like. In the examples shown, the light source 42 is a xenon-arc lamp and the fluid coolant 50 is water.

Figure 3:
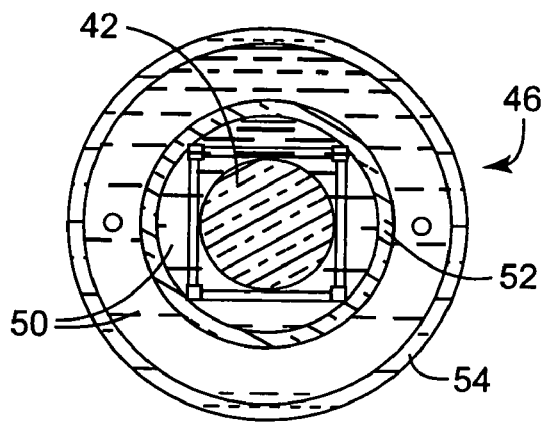
FIG. 3 shows a cross-section view of the illuminator of FIG. 2.

FIG. 3 shows a cross-section of the optical filter assembly 46 taken along line 3-3 of FIG. 2. In the example shown, the optical filter assembly 46 includes two optical filters, that is inner filter 52 and outer filter 54. The optical filters 52 and 54 are shown having a circular cross-section indicating that the filter assembly 46 is cylindrical. Other curvilinear or rectilinear shapes for the optical filters 52, 54 are contemplated. Coolant 50 flows in a first direction along the length of the illuminator 38 between the light source 42 and the inner filter 52. Coolant 50 flows in the opposite direction between the inner filter 52 and the outer filter 54. Other systems can include a cooling water inlet on one end and an outlet on the other.

Figure 4:
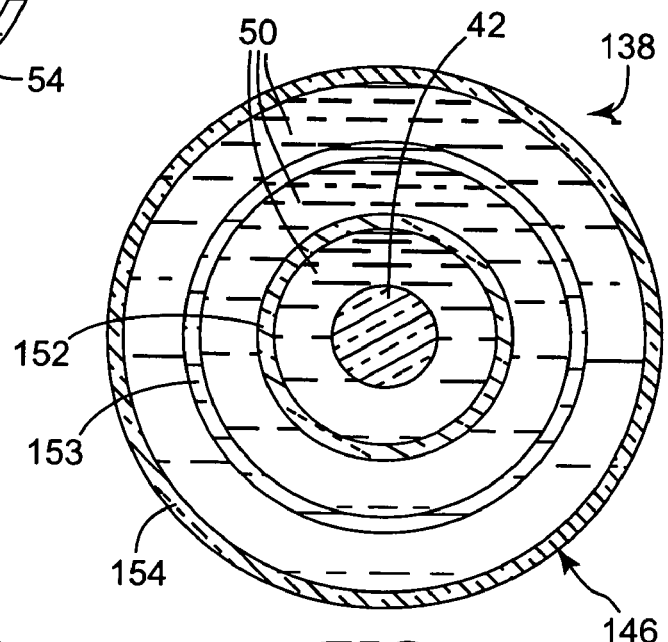
FIG. 4 shows a cross-section view of another example of an illuminator.

FIG. 4 shows a cross-section of another example of an illuminator 138 with an optical filter assembly 146, which includes three optical filters, that is inner filter 152, middle filter 153 and outer filter 154. Coolant 50 flows in a first direction along the length of the illuminator 138 between light source 42 and inner filter 152. The coolant flows in the opposite direction between both the inner filter 152 and middle filter 153 and middle filter 153 and outer filter 154.

Figure 5:
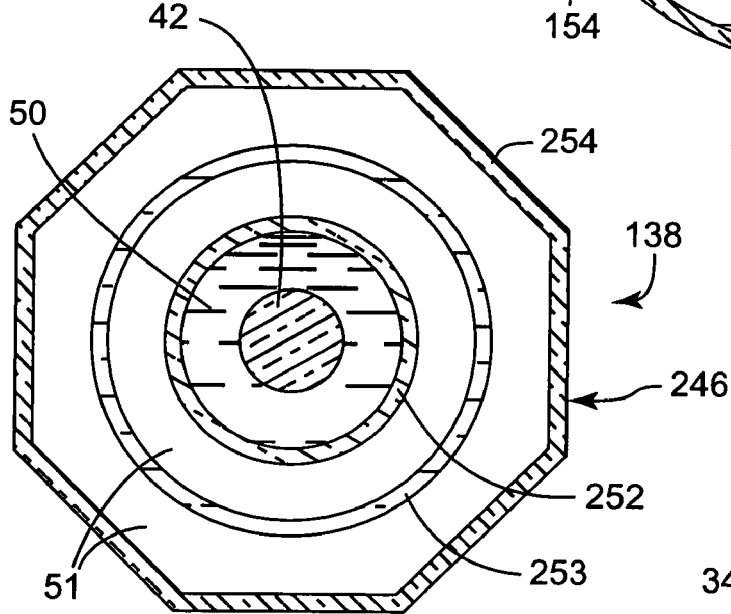
FIG. 5 shows a cross-section view of still another example of an illuminator.

FIG. 5 shows still another example of illuminator 238 with optical filter assembly 246 that includes three optical filters, that is inner filter 252, middle filter 253 and outer filter 254. In the example, a liquid coolant 50 such as water is passed in a first direction between the light source 42 and inner filter 252, and in the opposite direction between inner 252 and middle filter 253. A gaseous coolant 51 such as air is passed between the middle filter 253 and outer filter 254.

Figure 6:
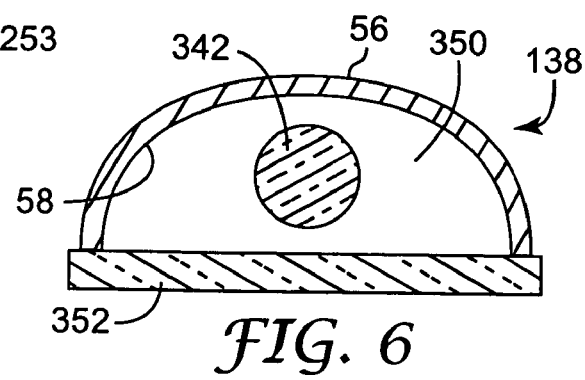
FIG. 6 shows a cross-section view of still another example of an illuminator.

FIG. 6 shows one example of an illuminator 338 that includes a single optical filter 352. In the example, the optical filter is a pane or flat filter and is connected to reflector 56 having a reflective concave surface 58. The combination of the reflector 56 and the optical filter 352 surrounds the light source 342. The illuminator 338 in the example is cooled with gaseous coolant 350 such as air. In this arrangement, the example is shown with a metal halide light source 342, although other light sources, such as xenon-arc light sources, are suitable for use in the illuminator 338. An illuminator with a single filter, rather than a plurality of filters, surrounding the light source and without a reflector is contemplated. Also, the use of a coolant other than a gaseous coolant is contemplated.

The illuminator may have various other shapes and sizes. Further, the optical filters in a filter assembly may be adjacent to or touching one another rather than spaced apart as shown. Other variations would be readily construed by one of ordinary skill in the art.

The optical filter assembly preferably includes a second filter prepared from a material that is ultraviolet transmissive. These filters do not substantially affect the advantageous simulation of terrestrial solar radiation. In one example, the ultraviolet transmissive optical filter has at least 60% light transmission at 250 nm and at 80% light transmission at 300 nm. The cut on wavelength for illumination passed through this optical filter assembly, including a lead glass optical filter and an ultra-violet transmissive optical filter, very closely approximates the cut on wavelength for the lead glass optical filter when used alone and is determined by the lead glass optical filter. One example of a material suitable for use in an ultraviolet transmissive optical filter is quartz glass having a thickness of 2 mm. Another example is a quartz glass with an infrared absorbing coating such as glass sold under the trade designation CIRA from ATLAS Material Testing Technology LLC of Chicago, Ill. having approximately the same thickness. Referring to FIG. 3, the inner filter 52 is constructed from a lead glass and the outer filter 54 is constructed from an ultraviolet transmissive glass such as quartz or quartz glass with an infrared absorbing coating. Alternatively, the inner filter 52 is constructed from the ultraviolet transmissive glass and the outer filter is constructed from lead glass.

Infrared absorbing coating on the quartz glass permits higher irradiance levels with a light source without a corresponding increase of the temperature of the product under test. One form of infrared control is with a water coolant. Another form of infrared control is the addition of an infrared absorbing material to the coolant. For example, cupric sulfates added to the water form an infrared absorbing coolant that begins absorbing light above 600 nm and matches the solar ultraviolet cut-on. Another form of infrared control is to use the glass with infrared absorbing coating in conjunction with the infrared absorbing coolant. Other examples of infrared control are known.

In order to improve the durability of the optical filter it is preferred that the optical filter proximate the light source comprises an opaque peripheral portion as described in U.S. patent application Ser. No. 10/454045, filed Jun. 4, 2003; incorporated herein by reference. A fitting is typically attached to the opaque peripheral portion and a polymeric material (e.g. adhesive) is disposed between the fitting and the opaque peripheral portion. The opaque peripheral portion shields the polymeric material from the illumination thereby reducing the rate of degradation.

Objects and advantages of the invention are further illustrated by the following examples, but the particular materials and amounts thereof recited in the examples, as well as other conditions and details, should not be construed to unduly limit the invention. All percentages and ratios herein are by weight unless otherwise specified.

EXAMPLES

Comp A-D and Examples 1-4 as follows depict the compositions of eight different glass compositions that were prepared and tested.

The samples of glass were prepared into blocks by Pegasus Glassworks Inc., Sturbridge, Mass. Each block, having approximate dimensions of 10 mm×35 mm×50 mm was cut into a 2 mm cross section using a 14" Model 1500 Dyna-Cut Precision Glass cut off saw. The glass samples were then ground flat using a 12" Heathway flat lapping wheel starting with a 74 micron disc, followed by a 40 micron disc, and then a 10 micron, each commercially available from 3M Company, St, Paul, Minn. under the trade designation "3M Diamond Lapping Disc". The final grind was with a 5 micron aluminum oxide disc commercially available from 3M Company under the trade designation "3M™ Trizact™ Fine Finishing Discs ". Each step in the grinding process was about a minute. The final polish was obtained using a slurry of cerium oxide on a polishing pad using the same Heathway lapping wheel for about a minute.

A pair of concentric disks, each having a 7 mm by 13 mm size opening in the center were machined for use as a holder for the 2 mm cross section glass sample. One of the disks had a recess about the opening to which the sample was affixed with aluminum tape at the periphery. The disks were placed together with the sample being sandwiched between the two disks. The assembly was then placed on the integrating sphere of a a spectroradiometer commercially available from Optronics (Orlando, Fla.) under the trade designation OL754 with OL754-PMT optics head and OL752S integrating sphere. The spectroradiometer was calibrated with a standard tungsten halogen lamp (Optronics OL752-10E or OL752-10J) with calibration traceable to National Institute for Standards and Technology (NIST). Spectral power distribution measurements were made from 250 to 400 nm at 2 nm increments or from 250 to 800 nm at 2 nm increments.

Figure 7:
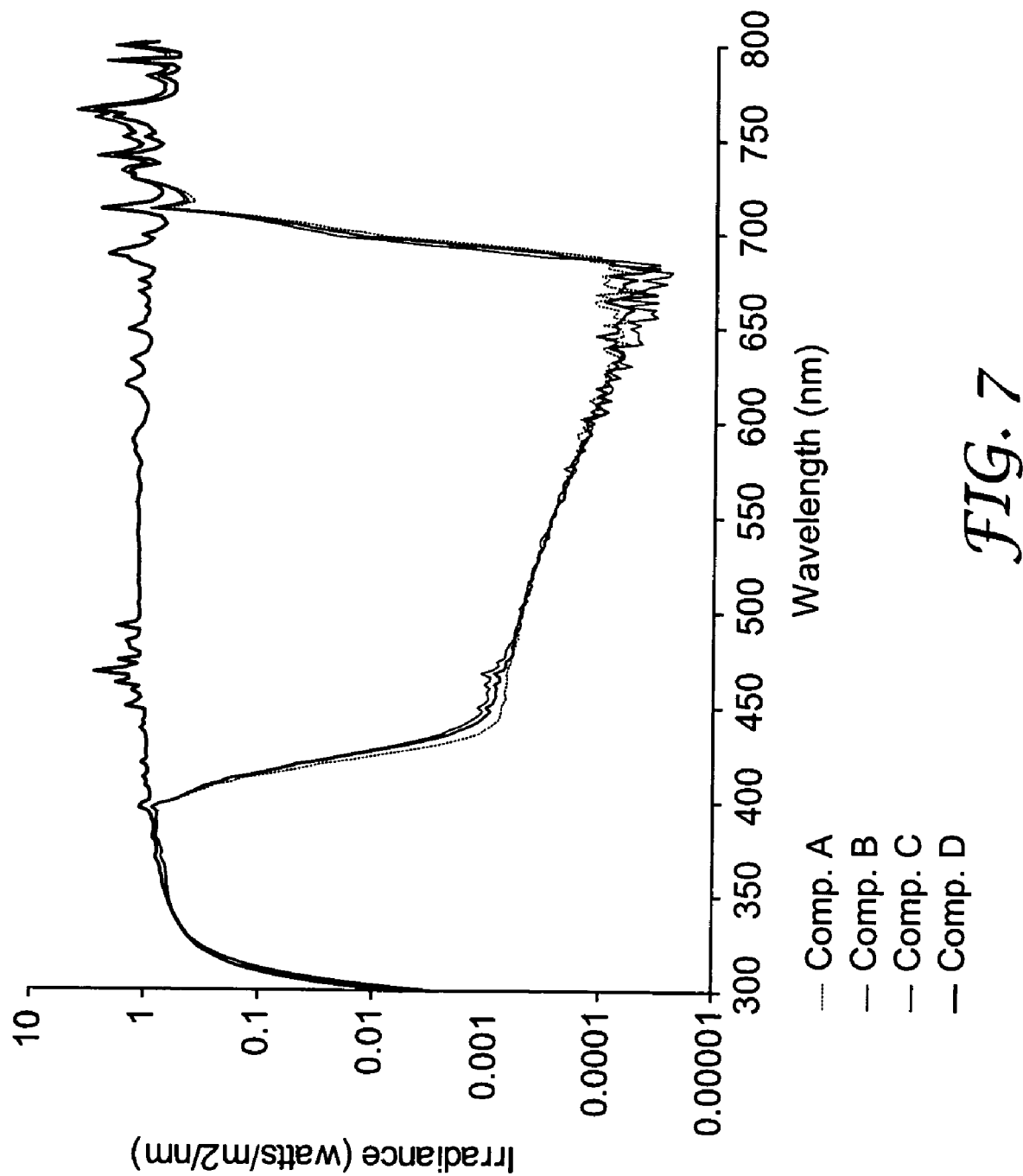
FIG. 7 shows a spectral power distribution of comparative examples.
Figure 8:
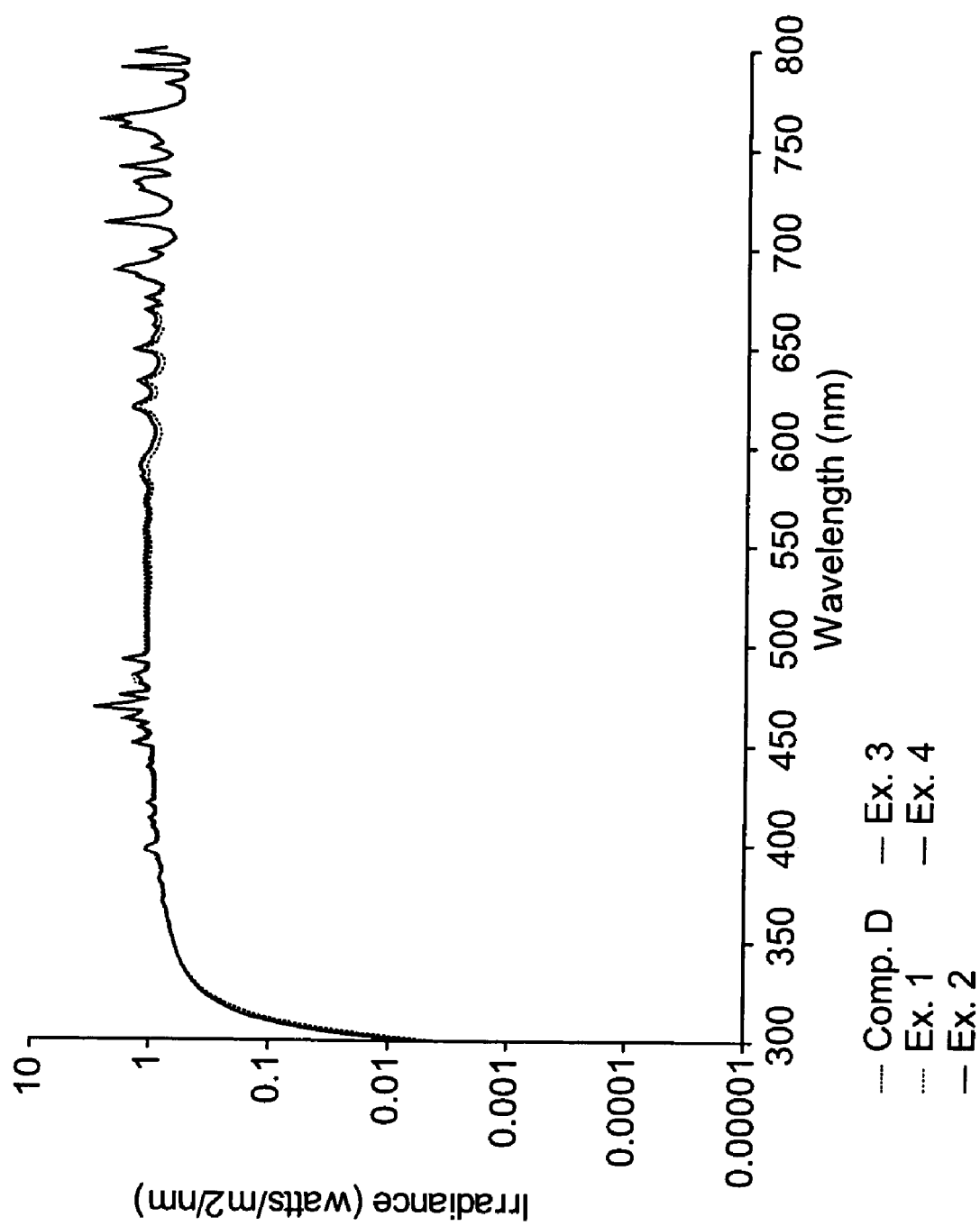
FIG. 8 shows a spectral power distribution of a comparative example in comparison to illustrative optical filters of the invention.

The results are depicted in FIGS. 7 and 8. FIG. 7 shows that Comp A, Comp B and Comp C each exhibit absorption of light between wavelengths of 400 and 700 nm. Such absorption will negate wavelengths of light that are present in natural sunlight and are important for determining for example the bleaching of yellow chromophores in cetain aromatic-containing polymers or the fading of visible light-sensitive pigments and dyes. Comp D, does not contain visible light absorbing components and thus does not exhibit such absorption. FIG. 8 shows that Examples 1-4 exhibits substantially the same spectral power distribution as Comp D. Accord-

|  | Comp A | Comp B | Comp C | Comp D |
|---|---|---|---|---|
| $SiO_2$ | 60.00 wt-% | 60.00 wt-% | 58.26 wt-% | 60.00 wt-% |
| $Na_2O$ | 9.64 | 10.96 | 9.36 | 9.64 |
| $K_2O$ | 8.61 | 9.79 | 8.36 | 8.61 |
| PbO | 19.00 | 16.50 | 21.36 | 21.74 |
| $Co_2O_3$ | 1.44 | 1.44 | 1.40 | none |
| NiO | 1.33 | 1.30 | 1.26 | none |
| Elemental Nickel | 0.86 wt-% | 0.84 wt-% | 0.812 wt-% |  |

|  | Example 1 | Example 2 | Example 3 | Example 4 |
|---|---|---|---|---|
| $SiO_2$ | 60.00 wt-% | 60.00 wt-% | 60.00 wt-% | 60.00 wt-% |
| $Na_2O$ | 9.64 | 9.64 | 9.64 | 9.64 |
| $K_2O$ | 8.62 | 8.62 | 8.62 | 8.62 |
| PbO | 21.74 | 21.74 | 21.74 | 21.74 |
| $Co_2O_3$ | 0.0051 | 0.0005 | none | none |
| NiO | none | none | 0.005 | 0.0005 |
| Elemental Nickel and/or Cobalt | 0.0036 wt-% 36 ppm | 0.00036 wt-% 36 ppm | 0.0032 wt-% 3.2 ppm | 0.00032 wt-% 3.2 ppm | ingly, very small concentrations of visible light absorbing components can be included in the glass of the optical filter.

Various modifications and combinations of the embodiments disclosed will be apparent to those skilled in the art, and those modifications are intended to be within the scope of the invention as defined in the appended claims.

What is claimed:

1. An accelerated weathering device comprising:
a weathering fixture adapted to hold at least one product sample;
an illuminator disposed proximate to the weathering fixture wherein the illuminator comprises a light source and an optical filter disposed proximate to the light source, the optical filter comprising a detectable amount of at least one visible light absorbing component in a total amount of less than 0.5 wt-% based on the total elemental concentration of the optical filter, the remainder of the optical filter comprises one or more inorganic oxides that do not absorb visible or ultraviolet light, and
wherein illumination passed through the optical filter has
a first ratio of total irradiance for wavelengths shorter than 290 nm to total irradiance for wavelengths ranging from 300 nm to 400 nm of less than $2.0 \times 10^{-6}$,
a second ratio of irradiance at 310 nm to total irradiance for wavelengths ranging from 300 nm to 400 nm of at least $1.2 \times 10^{-3}$, and
a third ratio of total irradiance at wavelengths ranging from 400 nm to 700 nm to total irradiance at wavelengths ranging from 290 nm to 800 nm of at least 0.6.

2. The accelerated weathering device of claim 1 wherein the illumination from the light source includes a spectral component of at least 290 nm to 400 nm.

3. The accelerated weathering device of claim 1 wherein the illumination from the light source includes irradiance ranging from about 0.3 W/m$^2$ to about 1.5 W/m$^2$ at 340 nm.

4. The accelerated weathering device of claim 1 wherein the optical filter is cylindrical.

5. The accelerated weathering device of claim 1 wherein the optical filter has a thickness of ranging from about 0.5 mm to about 10 mm.

6. The accelerated weathering device of claim 1 wherein the glass has a lead content of about 0.5% to about 50% by weight.

7. The accelerated weather device of claim 1 wherein the glass has a lead content of about 25% to about 35% by weight.

8. The accelerated weathering device of claim 1 wherein the optical filter comprises an ultraviolet transmissive optical filter operably coupled to the lead glass optical filter.

9. The accelerated weathering device of claim 8 wherein the ultraviolet transmissive optical filter comprises quartz glass.

10. The accelerated weathering device of claim 8 wherein the ultraviolet transmissive optical filter provides at least 60% transmission of light at 250 nm and at least 80% transmission of light at 300 nm.

11. The accelerated weathering device of claim 8 wherein the ultraviolet transmissive optical filter includes an infrared absorbing coating.

12. The accelerated weathering device of claim 8 including a plurality of ultraviolet transmissive optical filters.

13. The accelerated weathering device of claim 12 wherein the lead glass optical filter is disposed between two ultraviolet transmissive optical filters.

14. A method of accelerated weathering comprising:
providing at least one product sample proximate the illuminator in the accelerated weather device of claim 1, and radiating the product sample with the illuminator.

15. The method of claim 14 wherein the product sample is selected from the group consisting of paints, varnishes, protective coatings, plastics, textiles, signs, roofing materials, siding materials, window treatments, architectural ornaments, tapes, sealants, medications, adhesives, and water proofing treatments.

16. The method of claim 14 further comprising testing at least one product performance attribute after radiating the sample.

17. The accelerated weathering device of claim 1 wherein the amount of visible light absorbing components is less than 0.4 wt-%.

18. The accelerated weathering device of claim 1 wherein the amount of visible light absorbing components is less than 0.3 wt-%.

19. The accelerated weathering device of claim 1 wherein the amount of visible light absorbing components is less than 0.2 wt-%.

20. The accelerated weathering device of claim 1 wherein the amount of visible light absorbing components is less than 0.1 wt-%.

* * * * *

UNITED STATES PATENT AND TRADEMARK OFFICE
CERTIFICATE OF CORRECTION

PATENT NO.         : 7,400,445 B2                                          Page 1 of 1
APPLICATION NO.    : 11/141589
DATED              : July 15, 2008
INVENTOR(S)        : Richard M. Fischer, Jr.

It is certified that error appears in the above-identified patent and that said Letters Patent is hereby corrected as shown below:

On the Title Page Item (57)
Abstract, Delete "infared" and insert -- infrared --, therefor.

Column 2
Line 3, Delete "infared" and insert -- infrared --, therefor.

Column 8
Line 25, After "of a" delete "a". (Second Occurrence)
Line 39, Delete "cetain" and insert -- certain --, therefor.

Column 9
Line 44, In Claim 7, Delete "weather" and insert -- weathering --, therefor.

Signed and Sealed this

Seventh Day of October, 2008

JON W. DUDAS
*Director of the United States Patent and Trademark Office*